United States Patent [19]
Sikkema et al.

[11] Patent Number: 6,040,478
[45] Date of Patent: Mar. 21, 2000

[54] PROCESS FOR DICARBOXYLATING DIHYDRIC PHENOLS

[75] Inventors: Doetze Jakob Sikkema, Oosterbeek; Adrianus Maria Reichwein, Arnhem, both of Netherlands

[73] Assignee: Akzo Nobel N.V., Arnhem, Netherlands

[21] Appl. No.: 09/071,782

[22] Filed: May 1, 1998

Related U.S. Application Data

[63] Continuation of application No. PCT/EP96/04611, Oct. 21, 1996.

[30] Foreign Application Priority Data

Nov. 10, 1995 [NL] Netherlands ............ 1001628

[51] Int. Cl.⁷ .................................................. C07C 51/15
[52] U.S. Cl. ............................. 562/424; 562/423
[58] Field of Search ..................... 562/424, 423

[56] References Cited

U.S. PATENT DOCUMENTS

| | | |
|---|---|---|
| 2,816,137 | 12/1957 | Clemens, Jr. . |
| 3,448,145 | 6/1969 | Zorn et al. . |
| 3,646,131 | 2/1972 | Ikarasi . |
| 3,655,744 | 4/1972 | Yasuhara et al. . |

FOREIGN PATENT DOCUMENTS

| | | |
|---|---|---|
| 298289 | 1/1989 | European Pat. Off. . |
| 370389 | 5/1990 | European Pat. Off. . |
| 548906 | 6/1993 | European Pat. Off. . |
| 46-25374 | 7/1971 | Japan . |
| 46-25729 | 7/1971 | Japan . |
| 1108023 | 3/1968 | United Kingdom . |
| 1155776 | 6/1969 | United Kingdom . |
| WO 94/25506 | 11/1994 | WIPO . |

OTHER PUBLICATIONS

Derwent Patent Abstract 48885S–E (1971).
Derwent Patent Abstract 91–328591/45 (1991).
Derwent Patent Abstract 28893R (1970).
A.S. Lindsey et al., "The Kolbe–Schmitt Reaction", Chemical Reviews, vol. 57, pp. 583–620 (1957).
T.S. Gore et al., "Synthesis of Resorcinol–4, 6–& 2,4–Dicarboxylic Acids", Indian Journal of Chemistry, vol. 12, Sep. 1974, pp. 946–947.

*Primary Examiner*—Paul J. Killos
*Attorney, Agent, or Firm*—Richard P. Fennelly

[57] ABSTRACT

A process is disclosed for dicarboxylating dihydric phenols, notably those where the hydroxyl groups are in the para or the ortho position vis-à-vis one another. More particularly, the invention pertains to a process for preparing 2,5-dihydroxyterephthalic acid (2,5 DHTA). The invention comprises contacting a dihydric phenol with carbon dioxide in the presence of an alkali metal carbonate, the reaction being carried out in the presence of an alkali metal formate, at a temperature above the formate's melting point. The invention has several advantages over the well-known Kolbe-Schmitt reaction and other known carboxylation reactions, such as a lower operating pressure, higher yields, and/or shorter reaction times.

13 Claims, No Drawings

PROCESS FOR DICARBOXYLATING DIHYDRIC PHENOLS

This is a continuation of PCT/EP96/04611 filed Oct. 21, 1996.

The invention pertains to a process for dicarboxylating dihydric phenols. More particularly, the invention pertains to a process for preparing 2,5-dihydroxyterephthalic acid (2,5 DHTA).

The carboxylation of phenols by reacting alkali phenolate and carbon dioxide in a strongly alkaline medium (e.g., in KOH) is known under the name Kolbe-Schmitt reaction. See, for example, European Patent Publication Nos. 298, 289, 370,389, and 548,906. However, the preparation of dihydroxyterephthalic acid, the dicarboxylation product of hydroquinone, by means of this reaction can be effected only with low conversion and low yield.

For instance, British Patent No. 1,108,023 discloses a process for preparing 2,5 DHTA by means of a Kolbe-Schmitt reaction in a neutral solvent. The reagents comprise base, such as potassium carbonate, and carbon dioxide. The process gives a yield of from about 65% to over 90%, but it has the major drawback of requiring a very high pressure (the reaction takes place in an autoclave at from about 80 to about 110 atmospheres).

Other well-known processes for carboxylating phenols likewise are attended with drawbacks, e.g., objectionably high pressure, lengthy reaction time, low yield, or they are not suitable for dicarboxylation in any case.

For instance, it is known from *Chemical Reviews* Vol. 57 (1957), at p. 585, to carboxylate di- and trihydric phenols in an alkaline (aqueous) solution. This is a process employing solutions of, say, alkali bicarbonate, usually with the use of carbon dioxide at atmospheric pressure. The method, which is stated to be suitable only for the more reactive di- and trihydric phenols, such as resorcinol, results in monocarboxylation. The invention envisages a dicarboxylation process which can also be used in the case of dihydric phenols where the hydroxyl groups are in the para or the ortho position vis-à-vis one another (which phenols do not belong to the group of more reactive phenols and are far less reactive than resorcinol).

Incidentally, a process for dicarboxylating resorcinol is known from the *Indian Journal of Chemistry,* Vol. 12, September 1974, pp. 946–947. By reacting resorcinol and dry potassium bicarbonate at elevated temperature (210° C.), the corresponding 4,6-dicarboxylic acid is formed. The manner in which the reaction is carried out, only on analytical scale in a Carius tube (a sealed tube of 1 by 2.5 cm), shows that it is unsuitable for scaling up, let alone for use on any remotely commercially acceptable scale, this also in view of the fact that the reaction product obtained is in the form of a rock hard lump.

Japanese Hei-3-218919 pertains to the preparation of hydroxybenzoic acid by monocarboxylating phenol, in which process sodium phenolate, sodium carbonate, carbon dioxide, and sodium formate are combined in an autoclave and the whole is left to react for thirteen hours at 260° C. under a pressure of 75 bar.

Japanese Sho-46-25729 pertains to the preparation of hydroxytrimesylic acid by dicarboxylating salicylic acid or p-hydroxybenzoic acid, in which process the disodium salt or dipotassium salt of one of the aforementioned acids is reacted with carbon dioxide in the presence of alkali carbonate and sodium formate or potassium formate, at a temperature above the melting point of the formate, and under a pressure generally amounting to 50–250 bar. It is true that on rare occasions a pressure of only 2 bar is employed, but in that case the reaction time required is over forty hours and the yield a mere 60%.

From Japanese Sho-46-25374 it is known to add a second carboxyl group to m-hydroxybenzoic acid by reacting the corresponding potassium salt with potassium carbonate and carbon dioxide in the presence of potassium formate. In this way monohydroxyterephthalic acid is prepared under a pressure up to 50 atmospheres and by means of reaction over a period of twenty-four hours.

British Patent No. 1,155,776 deals with the carboxylation of various aromatic alcohols using carbon monoxide and alkali carbonate. This reaction has a low yield and the conditions are uneconomical. For instance, hydroquinone is carboxylated under a pressure of 54 bar, with 0.3 g of 2,5-dihydroxyterephthalic acid being formed from 5.5 g of hydroquinone. The selectivity of this reaction to the desired product is low: the largest portion by far of the reaction product, 4.5 g, is formed by the monocarboxylic acid 2,5-dihydroxybenzoic acid. A comparable publication is Japanese Patent Publication No. A 70/10933.

From U.S. Pat. No. 3,646,131 it is known to convert a monocarboxylic acid, such as formic acid, into a dicarboxylic acid, such as oxalic acid, by reaction with alkali carbonate and carbon monoxide. This patent does not deal with dicarboxylating phenols.

U.S. Pat. No. 3,655,744 describes the carboxylation of metal aryloxides with carbon monoxide and a carboxylating agent consisting of a metal salt of carbonic acid, e.g., potassium carbonate.

Another background art reference is U.S. Pat. No. 2,816, 137. This patent discloses a deviation from the Kolbe synthesis which amounts to employing hydroxy aromatic carboxylic esters rather than phenols as starting compounds.

It is desired to prepare 2,5-DHTA, which is a monomer for rigid rod polymers as described in PCT Patent Publication No. WO 94/25506 and a starting material for various colorants and fluorescent materials, in an economically advantageous manner and also with as little waste material as possible being produced. The invention accordingly has for its object to provide a process for the preparation of 2,5-DHTA, and other dicarboxylation products of para- or ortho-dihydric phenols, under favorable conditions, notably a not too high or even atmospheric pressure, in a comparatively short reaction time, and with the desired product being obtained with a high selectivity and in a high, even quantitative yield.

Surprisingly, it was found that dihydric phenols, including those where the hydroxyl groups are in the para or the ortho position vis-à-vis one another, can be di-carboxylated using a process which comprises contacting a dihydric phenol with carbon dioxide in the presence of an alkali metal carbonate, with the reaction being carried out in the presence of an alkali metal formate at a temperature above the formate's melting point. The reaction can be carried out under very favorable conditions, to give good selectivity and a high yield. Furthermore, the reaction is suitable for use on a commercial scale.

The melted formate was found to have an essentially favorable effect on the reaction, probably because it can function, for example, as a strongly polar solvent. In this connection, it is preferred that the alkali metal formate employed is potassium formate, since it has a comparatively low melting point (167° C.), making it possible for the reaction to be carried out at a favorable temperature (from about 160° C., the melting point in the reaction mixture is lowered in relation to pure formate). Compared with the well-known Kolbe-Schmitt reaction and other familiar carboxylating reactions the invention offers significant advantages, such as a lower operating pressure, a higher yield, and/or a shorter reaction time. Further, the reaction exhibits a relatively low sensitivity for the presence of water, a consequence of which is, for example, that one can start from the phenol itself rather than a phenolic salt. This is an advantage, in view of the phenolic salt being extremely sensitive to air.

Further essential reagents in the process according to the present invention are the carbon dioxide and the carbonate. Instead of carbon dioxide and alkali metal carbonate being added separately, very suitable use can be made of alkali metal bicarbonate ($MHCO_3$), for it splits up in situ into alkali metal carbonate ($M_2CO_3$) and $CO_2$. If the reaction is carried out in this manner, it is preferred to employ an operating pressure of about 5 to 15 bar, since otherwise a portion of the $CO_2$ introduced in the form of bicarbonate will escape. It will then have to be collected separately to yet be pumped into the reactor. Preferably, however, carbon dioxide and carbonate are employed separately, since this will make it possible to carry out the reaction at a pressure of 1–2 bar at the most and it will also be possible to operate under atmospheric pressure.

Both in the embodiment where carbon dioxide and carbonate are used separately and in the embodiment where the carbon dioxide and the base are used in the form of alkali metal bicarbonate, it is preferred for improved progress of the reaction and lower potassium salt melting points to use potassium carbonate or potassium bicarbonate as the carbonate.

Dihydric phenols which can be carboxylated according to the present invention are not only the more reactive dihydric phenols where the hydroxyl groups are in the meta position vis-à-vis one another, but also, and especially, those where the hydroxyl groups are in the para or the ortho position vis-à-vis one another. These include hydroquinone (p-dihydroxybenzene), from which, according to the invention, 2,5-DHTA is prepared, pyrocatechol (o-dihydroxybenzene), from which 2,3-DHTA is formed, and analogous polynuclear aromatic dihydric phenols, from which the corresponding polynuclear aromatic dihydroxydicarboxylic acids can be prepared.

As was stated earlier, the process according to the present invention relates in particular to the preparation of 2,5-dihydroxyterephthalic acid. In this process use is made of hydroquinone as dihydric phenol, and the resulting dialkali metal salt is worked up in a known manner. The reaction preferably comprises contacting hydroquinone with potassium carbonate and carbon dioxide, optionally in the form of potassium bicarbonate, with the reaction being carried out in the presence of potassium formate at a temperature above 160° C., preferably 175–225° C. The resulting dipotassium salt of 2,5-DHTA is formed in a few hours at the most (three to four hours), in a quantitative yield. If it is desired to work up the dipotassium salt to the corresponding dicarboxylic acid, one suitable method comprises crystallization from water added on conclusion of the reaction. In this process potassium formate remains in solution in the filtrate, which can easily be boiled down and then re-used.

In the preparation of 2,5-DHTA it is preferred to use 1 to 20 g, more preferably 2 to 6 g, of potassium formate per gram of hydroquinone. For each mole of dihydric phenol that is used, preferably 2–5 moles, more particularly 2–3 moles, of alkali metal bicarbonate are employed, alternatively in the form of 1–1,5 moles of alkali metal carbonate and 1–1,5 moles of carbon dioxide. For that matter, the amount of carbon dioxide can be unrestricted.

The invention will be illustrated with reference to the following, nonlimiting Examples below.

EXAMPLE 1

In this Example, 22.22 g of hydroquinone followed by 86.55 g of p-xylene were combined with 47.55 g of $KHCO_3$, 62.10 g of HCOOK, and 1.97 g of $K_2CO_3$ in a 300 ml autoclave (stainless steel, turbine stirrer, no baffles). The air was displaced by nitrogen; under a nitrogen blanket of 6.0 bar heating and stirring was commenced. After forty minutes, at a temperature of 137° C., the contents of the reactor took ten minutes to melt before a further increase in their temperature: ten minutes later the temperature reached 204° C., and the reaction mixture was stirred for three hours at 198° C. ($T_{max}$ 211° C. at seven minutes into the three-hour period before settling down to 198° C.; $P_{max}$ 19.8 bar). After cooling to 73° C., a mixture of 100 ml of water and 0.59 g of sodium sulfite was added after the reactor had been opened: it should be noted that the reaction mass consisted of a frozen melt (broken into lumps at and above the level of the stirring apparatus) underneath a layer of xylene. The reactor was closed again, heated to 129° C., and cooled to room temperature. A rich slurry was collected. Analysis (capillary zone electrophoresis) of the reaction mixture indicated that the conversion of the reaction mixture into DHTAK2 exceeded 95%, the remainder being the potassium salt of dihydroxybenzoic acid.

EXAMPLE 2

A glass reactor equipped with a U-shaped stirrer and a thermocouple was filled with a mixture of hydroquinone (22.33 g, 0.20 mole), potassium carbonate (31.36 g, 0.23 mole), and potassium formate (45.54 g) and flushed three times (vacuum/$CO_2$). The reaction mixture was heated to 200° C. under 1.2 bar $CO_2$ for four hours. The pale yellow, doughy product was dissolved in 1 l of boiling water containing 0.5% $Na_2SO_3$ and was precipitated with concentrated hydrochloric acid. The bright yellow product, 2,5-dihydroxyterephthalic acid (2,5-DHTA), was filtered off and dried under vacuum at 50° C. The yield was 44.14 g (0.20 mole, 100%).

EXAMPLE 3

In a glass reactor having a bottom outlet and equipped with a spiral-shaped stirrer and a thermocouple potassium formate (329 g) was melted under vacuum. When the temperature of the melt reached 190° C., the reactor was aerated with $CO_2$ and potassium carbonate (125.04 g, 0.906 mole) and hydroquinone (80.06 g, 0.728 mole) were added to the melt. The reaction mixture was stirred at 200° C. under 1.5 bar $CO_2$ for four and one-half hours. Then 250 ml of water were added to the reaction mixture, and the slurry was removed from the reactor and crystallized from 3.5 l of boiling water. After cooling, the product was filtered off and washed with ice water. Drying under vacuum at 100° C. produced 87% of pale yellow dipotassium 2,5-dihydroxyterephthalate ($K_2$-2,5-DHTA, 173.77 g, 0.634 mole). The filtrate was boiled down and the residue was reused in a carboxylating reaction using potassium carbonate (95.90 g, 0.695 mole) and hydroquinone (75.06 g, 0.682 mole). According to the above specification, 98% pale yellow $K_2$-2,5-DHTA (184.31 g, 0.673 mole) was obtained. Repetition of this recycle process using potassium carbonate (94.14 g, 0.682 mole) and hydroquinone (75.16 g, 0.683 mole) according to the above specification produced 95% pale yellow $K_2$-2,5-DHTA (178.65 g, 0.652 mole).

EXAMPLE 4

A glass reactor equipped with a U-shaped stirrer and a thermocouple was filled with a mixture of resorcinol (25.06 g, 0.228 mole), potassium carbonate (39.55 g, 0.287 mole), and potassium formate (50.73 g) and flushed three times (vacuum/$CO_2$). The reaction mixture was heated to 200° C. under 1 bar $CO_2$ for five and one-half hours. The pale red, doughy product was dissolved in 1 l of boiling water containing 0.5% $Na_2SO_3$ and precipitated with concentrated hydrochloric acid. The product, 4,6-dihydroxyisophthalic acid (4,6-DHIA), was filtered off and dried under vacuum at 50° C. The yield was 37.52 g (0.189 mole, 83%).

What is claimed is:

1. A process for dicarboxylating dihydric phenols which comprises contacting the phenol with carbon dioxide in the presence of alkali metal carbonate, characterized in that the reaction is carried out in the presence of an alkali metal formate, at a temperature above the melting point of the formate.

2. A process according to claim 1, characterized in that the alkali metal formate used is potassium formate.

3. A process according to either claim 1 or 2, characterized in that the carbon dioxide and the carbonate are employed in the form of alkali metal bicarbonate.

4. A process according to claim 3, characterized in that 2–5 moles of bicarbonate are employed per mole of dihydric phenol.

5. A process according to either claim 1 or 2, characterized in that carbon dioxide and carbonate are used separately.

6. A process according to claim 5, characterized in that per mole of dihydric phenol 1.0–1.5 moles of carbonate and 1.0 to 1.5 moles of carbon dioxide are employed.

7. A process according to claim 5, characterized in that the carbonate used is potassium carbonate.

8. A process according to claim 6, characterized in that the carbonate used is potassium carbonate.

9. A process according to any one of claims 1–2, 4, or 6–8, characterized in that it is used with phenols where the hydroxyl groups are in the para or the ortho position vis-à-vis one another.

10. A process according to claim 3, characterized in that the carbon dioxide and the carbonate are employed in the form of alkali metal bicarbonate, and it is used with phenols where the hydroxyl groups are in the para or the ortho position vis-à-vis one another.

11. A process according to claim 5, characterized in that carbon dioxide and carbonate are used separately and it is used with phenols where the hydroxyl groups are in the para or the ortho position vis-à-vis one another.

12. A process for the preparation of 2,5-dihydroxyterephthalic acid in which hydroquinone is contacted with potassium carbonate and carbon dioxide, characterized in that the reaction is carried out in the presence of an alkali metal formate, at a temperature above the melting point of the formate.

13. A process according to claim 12, characterized in that the alkali metal formate used is potassium formate and 1 to 20 g of it are employed per gram of hydroquinone.

* * * * *